(12) United States Patent
Couturier et al.

(10) Patent No.: US 8,884,041 B2
(45) Date of Patent: Nov. 11, 2014

(54) METHOD FOR SYNTHESIZING AN OMEGA-AMINO ACID OR ESTER FROM A MONOUNSATURATED FATTY ACID OR ESTER

(75) Inventors: Jean-Luc Couturier, Lyons (FR); Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/234,879

(22) PCT Filed: Jul. 26, 2012

(86) PCT No.: PCT/FR2012/051770
§ 371 (c)(1),
(2), (4) Date: Feb. 4, 2014

(87) PCT Pub. No.: WO2013/017782
PCT Pub. Date: Feb. 7, 2013

(65) Prior Publication Data
US 2014/0187808 A1    Jul. 3, 2014

(30) Foreign Application Priority Data
Aug. 1, 2011    (FR) ..................................... 11 57020

(51) Int. Cl.
| | | |
|---|---|---|
| *C07C 227/00* | (2006.01) | |
| *C07B 43/00* | (2006.01) | |
| *C07C 229/08* | (2006.01) | |
| *C07C 227/04* | (2006.01) | |
| *C07C 227/08* | (2006.01) | |

(52) U.S. Cl.
CPC ............. *C07C 227/08* (2013.01); *C07C 229/08* (2013.01); *C07C 227/04* (2013.01)
USPC ........................................................ 554/114

(58) Field of Classification Search
CPC .... C07C 227/04; C07C 227/08; C07C 227/26
USPC ........................................................... 554/114
See application file for complete search history.

(56) References Cited

U.S. PATENT DOCUMENTS

2011/0224454 A1    9/2011   Dubois

FOREIGN PATENT DOCUMENTS

| GB | 741739 A | 12/1955 | |
|---|---|---|---|
| WO | WO 2010/055273 A1 | 5/2010 | |
| WO | WO 2010055273 A1 * | 5/2010 | ............ C07C 229/08 |

OTHER PUBLICATIONS

International Search Report (PCT/ISA/210) mailed on Oct. 11, 2012, by the French Patent Office as the International Searching Authority for International Application No. PCT/FR2012/051770.

* cited by examiner

*Primary Examiner* — Deborah D Carr
(74) *Attorney, Agent, or Firm* — Buchanan Ingersoll & Rooney P.C.

(57) ABSTRACT

A method for synthesizing ω-amino-alkanoic acids or the esters thereof from natural unsaturated fatty acids passing through an intermediate ω-unsaturated nitrile compound. The method is simple to implement and, relative to known methods, avoids the environmental constraints and economic disadvantages resulting from the reaction by-products. The method includes synthesizing an ω-amino acid (ester) of formula R3OOC—(CH2)q-CH2NH2, in which R3 is H or an n-butyl radical and q is an integral index of between 2 and 13, from a monounsaturated fatty acid (ester) of formula (R1-CH=CH—(CH2)p-COO)xR2, in which x represents 1, 2 or 3, R1 is H or a hydrocarbon radical comprising from 4 to 11 carbon atoms and, where appropriate, a hydroxyl function, R2 is H or an alkyl radical comprising from 2 to 4 carbon atoms, and may contain one or more heteroatoms, and p is an integral index of between 2 and 11, including a reaction step of ammoniation.

5 Claims, No Drawings

METHOD FOR SYNTHESIZING AN OMEGA-AMINO ACID OR ESTER FROM A MONOUNSATURATED FATTY ACID OR ESTER

The work which led to this invention received financial support from the European Union as part of Framework Program 7 (FP7/2007-2013) under project number 241718 EUROBIOREF.

The invention is directed to a process for synthesizing ω-amino-alkanoic acids or their esters from unsaturated natural fatty acids, proceeding via an ω-unsaturated nitrile intermediate compound.

The polyamides industry uses a whole range of monomers consisting of long-chain ω-amino acids, normally called Nylon, which are characterized by the length of methylene chain $(-CH_2)_n$ separating two $-CO-NH-$ amide functions. Known accordingly are Nylon-6, Nylon 6-6, Nylon 6-10, Nylon 7, Nylon 8, Nylon 9, Nylon 11, Nylon 13, etc.

These monomers are manufactured, for example, by a chemical synthesis route using, in particular, as starting material, C2 to C4 olefins, cycloalkanes or benzene, but also castor oil (Nylon 11), erucic oil or lesquerolic oil (Nylon 13), etc.

The current development with regard to the environment is resulting, in the fields of energy and chemistry, in favoring the development of natural raw materials originating from a renewable source. This is the reason why some studies have been commenced to develop, industrially, processes which use fatty acids/esters as a raw material for manufacturing these monomers. There are only a few industrial examples of this type of approach. One of the rare examples of an industrial process utilizing a fatty acid as raw material is that of the manufacture, from the ricinoleic acid extracted from castor oil, of 11-aminoundecanoic acid, which forms the basis for the synthesis of Rilsan 11®. This process is described in the work "Les Procédés de Pétrochimie" by A. Chauvel et al., published in Editions TECHNIP (1986). 11-Aminoundecanoic acid is obtained in a number of steps. The first involves methanolysis of the castor oil in basic medium, producing methyl ricinoleate, which is subsequently subjected to pyrolysis to give heptanaldehyde on the one hand and methyl undecylenate on the other. The latter is converted to acid form by hydrolysis. The acid formed is subsequently subjected to hydrobromination to give the ω-brominated acid, which is converted by amination to 11-aminoundecanoic acid. The principal studies have related to the synthesis of 9-aminononanoic acid, which is the precursor of Nylon 9, from oleic acid of natural origin.

With regard to this particular monomer, it is possible to cite the work "n-Nylons, Their Synthesis, Structure and Properties"—1997, published by J. Wiley and Sons, in which section 2.9 (pages 381 to 389) is devoted to 9-Nylon. This article summarizes the accomplishments and studies carried out on the subject. Mention is made therein, on page 381, of the process developed by the former Soviet Union, which led to the commercialization of Pelargon®. Mention is also made therein, on page 384, of a process developed in Japan that uses oleic acid originating from soybean oil as starting material. The corresponding description refers to the work by A. Ravve "Organic Chemistry of Macromolecules" (1967), Marcel Dekker, Inc., in which section 15 is devoted to polyamides, referring to the existence of such a process on page 279.

In order to be fully informed with regard to the state of the art on this subject, it is necessary to cite the many articles published by E. H. Pryde et al. between 1962 and 1975 in Journal of the American Oil Chemists' Society—"Aldehydic Materials by the Ozonization of Vegetable Oils" Vol. 39 pages 496-500; "Pilot Run, Plant Design and Cost Analysis for Reductive Ozonolysis of Methyl Soyate" Vol. 49 pages 643-648; and R. B. Perkins et al. "Nylon-9 from Unsaturated Fatty Derivatives: Preparation and Characterization", JAOCS, Vol. 52 pages 473-477. It should be noted that the first of these articles also refers, on page 498, to prior studies carried out by Japanese authors: H. Otsuki and H. Funahashi.

To summarize this part of the state of the art concerning this type of synthesis of "Nylon 9" from vegetable oils, a description may be given of the simplified reaction mechanism below, applied to the oleic ester, which is extracted from the oils by methanolysis:

Reductive Ozonolysis

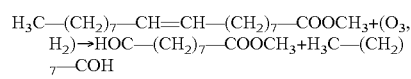

Reductive Amination

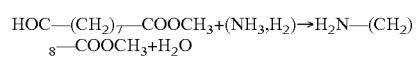

Hydrolysis

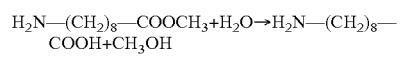

This route, though very attractive from a reaction standpoint, nevertheless exhibits a substantial economic disadvantage arising from the production, during the first step, of a long-chain aldehyde (9 carbon atoms in total) that has virtually no derivable value, particularly in the polyamide polymers industry. UK patent No. 741,739, for its part, describes the synthesis of this same acid from oleic acid, but using the oleonitrile route. The simplified reaction scheme of this process is that below. An analogous route is cited in the aforementioned article by R. B. Perkins et al., page 475.

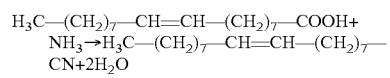

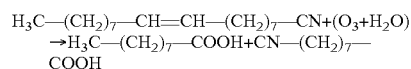

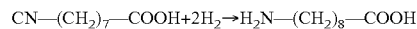

This synthesis leads to pelargonic acid, $H_3C-(CH_2)_7-COOH$, as a by-product. The aim of the present invention is to provide a new process for synthesizing a whole range of ω-amino-alkanoic acids or their esters from unsaturated natural fatty acids.

The problem is therefore to find a process for synthesizing various ω-amino acids of formula $H_2N-(CH_2)_n-COON$ (and their polymers) in which n is between 3 and 14 from renewable raw materials (very widely available and therefore relatively inexpensive) that is simple to implement while avoiding, on the one hand, the environmental constraints set out above and, on the other hand, the economic disadvantages caused by the by-products of the reactions.

The proposed solution involves working from raw materials consisting of natural, long-chain, unsaturated fatty acids, converting them, in a first stage, into ω-unsaturated nitriles, and then, in a second stage, "reinserting" a carboxylic acid function into the compound by acting on the terminal double bond of the ω-unsaturated nitrile, by a cross metathesis reaction with an acrylate compound.

A natural fatty acid is an acid from the plant or animal spheres, including algae, more generally from the plant kingdom, which is therefore renewable. This acid will comprise at least one olefinic unsaturation, the location of which in position x relative to the acid group (delta x), and comprising at least 10 and preferably at least 14 carbon atoms per molecule, will determine the formula of the final ω-amino acid.

Examples of such acids include the C10 acids, obtusilic (cis-4-decenoic) acid and caproleic (cis-9-decenoic) acid, the C12 acids, lauroleic (cis-9-dodecenoic) acid and linderic (cis-4-dodecenoic) acid, the C14 acids, myristoleic (cis-9-tetradecenoic) acid, physeteric (cis-5-tetradecenoic) acid and tsuzuic (cis-4-tetradecenoic) acid, the C16 acid, palmitoleic (cis-9-hexadecenoic) acid, the C18 acids, oleic (cis-9-octadecenoic) acid, elaidic (trans-9-octadecenoic) acid, petroselinic (cis-6-octadecenoic) acid, vaccenic (cis-11-octadecenoic) acid and ricinoleic (12-hydroxy-cis-9-octadecenoic) acid, the C20 acids, gadoleic (cis-9-eicosenoic) acid, gondoic (cis-11-eicosenoic) acid, cis-5-eicosenoic acid and lesquerolic (14-hydroxy-cis-11-eicosenoic) acid, and the C22 acids, cetoleic (cis-11-docosenoic) acid and erucic (cis-13-docosenoic) acid.

These various acids are obtained from vegetable oils extracted from a variety of oil-bearing plants, such as sunflower, oilseed rape, castor oil plant, bladderpod, olive, soya, palm tree, avocado, sea buckthorn, coriander, celery, dill, carrot, fennel, camelina, and Limnanthes alba (meadowfoam).

They are also obtained from the terrestrial or marine animal worlds, and, in the latter case, in the forms equally of fish, of mammals, and of algae. In general they are fats originating from ruminants, from fish such as cod, or from marine mammals such as whales or dolphins.

The invention is directed to a process for synthesizing an ω-amino acid (ester) of formula $R_3OOC-(CH_2)_q-CH_2NH_2$, in which R3 is H or a n-butyl radical and q is an integral index of between 2 and 13, from a monounsaturated fatty acid (ester) of formula $(R_1-CH=CH-(CH_2)_p-COO)_xR_2$, in which x represents 1, 2 or 3, $R_1$ is H or a hydrocarbon radical comprising from 4 to 11 carbon atoms and, where appropriate, a hydroxyl function, $R_2$ is H or an alkyl radical comprising from 2 to 4 carbon atoms, and may contain one or more heteroatoms, and p is an integral index of between 2 and 11, comprising a reaction step of ammoniation, leading to the conversion of the carbonyl function to a nitrile function, characterized in that:

in a first stage, the unsaturated fatty acid/ester is converted into an ω-unsaturated nitrile of formula $CH_2=CH-(CH_2)_p-CN$ in two successive steps (in any order) of ethenolysis and ammoniation, and then in a second stage, this ω-unsaturated nitrile is converted into an ester nitrile of formula $R_3OOC-CH=CH-(CH_2)_p-CN$, in which $R_3$ is n-butyl, by a cross metathesis reaction of the ω-unsaturated nitrile with an acrylate of formula $CH_2=CH-COOR_3$, with a catalyst of formula (I),

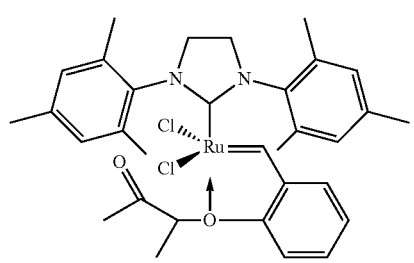

(I)

and then in a third stage, the ester nitrile is hydrogenated to ω-amino acid (ester) of formula $ROOC-(CH_2)_q-CH_2NH_2$.

The reaction procedure is, then, as follows:

First Stage:

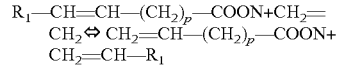

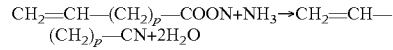

or, inverting the order of the reactions,

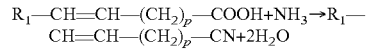

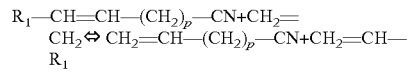

Second Stage:

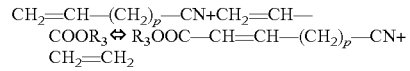

Third Stage:

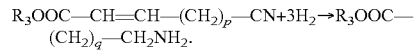

In this embodiment of the process, q is equal to p+2.
Applied to oleic acid, the procedure becomes
First Stage:

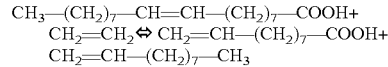

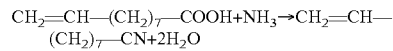

or, inverting the order of the reactions,

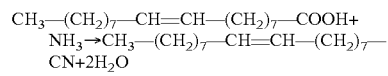

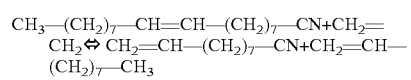

Second Stage:

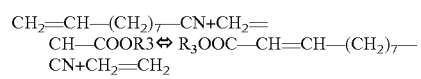

Third Stage:

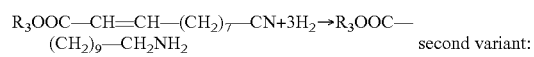

second variant:

The only "by-products" formed are a long-chain α-olefin, possibly comprising a hydroxyl function.

In a simplified variant embodiment of the process of the invention, a step may be saved by synthesizing the nitrile of the fatty acid/ester, of formula $R_1-CH=CH-(CH_2)_p-CN$, in the first stage, by ammoniation of the original acid/ester, then by subjecting the latter to cross metathesis with an acrylate $R_3OOC-CH=CH_2$ to give the ester nitrile of formula $R_3OOC-CH=CH-(CH_2)_p-CN$, which will be subsequently hydrogenated to $R_3OOC-(CH_2)_{p+2}-CH_2NH_2$.

In another variant of the process, using hydroxyl-containing fatty acids as raw material, such as ricinoleic acid and lesquerolic acid, which conform to the general formula $R_1-CH=CH-(CH_2)_p-COON$ with $R_1$ being $CH_3-(CH_2)_5CHOH-CH_2-$ and p being, respectively, 7 and 9, the acid in its methyl ester form is subjected to pyrolysis, giving an ω-unsaturated ester of formula $CH_2=CH-(CH_2)_{p+1}-COOCH_3$, which is converted, directly or proceeding via the acid, into an ω-unsaturated nitrile of the same kind as the intermediate compound obtained at the end of the first stage of the process described above. This variant therefore involves, for these particular fatty acids, replacing the initial ethenolysis by a pyrolysis.

The following stages of the process are analogous to those of the process described above. They therefore result in compounds of formula $R_3OOC-(CH_2)_q-CH_2NH_2$ in which q is equal to p+3.

Accordingly, in preferred embodiments of the invention:
in the first stage the ethenolysis of the acid (ester) is carried out first, followed by the ammoniation of the ω-alkenoic acid;
in the first stage, the ammoniation of the acid (ester) is carried out first, followed by the ethenolysis of the nitrile of the starting fatty acid;
in the first stage the pyrolysis of the hydroxyl-containing fatty acid (ester) is carried out first of all, followed by the ammoniation of the ω-alkenoic acid (ester) obtained from the pyrolysis;
in the first stage the ammoniation of the acid (ester) is carried out, without continuing to the ethenolysis reaction;
in the second stage, the product obtained from the first stage is subjected to a cross metathesis reaction with the acrylate compound;
the compound obtained from the second stage is subjected to a hydrogenation.

In one particular embodiment of the invention, in the formula $(R_1-CH=CH-(CH_2)_p-COO)_xR_2$, x represents 3 and the radical R2 is $CH_2-CH-CH_2$, or x represents 2 and $R_2$ is $CH_2-CH-CH_2OH$ or $CH_2-CHOH-CH_2$.

Metathesis reactions have been known for a long time, although their industrial applications are relatively limited. With regard to their use in the conversion of fatty acids (esters), reference may be made to the article by J. C. Mol "Catalytic metathesis of unsaturated fatty acid esters and oil" in Topics in Catalysis of unsaturated fatty esters and oil Vol. 27, Nos. 1-4, February 2004 (Plenum Publishing).

Catalysis of the metathesis reaction has been the subject of a very large number of works, and the development of sophisticated catalytic systems. Mention may be made, for example, of the tungsten complexes developed by Schrock et al. (J. Am. Chem. Soc. 108 (1986) 2771 or Basset et al., Angew. Chem., Ed. Engl. 31 (1992) 628. More recently, catalysts have appeared which are referred to as Grubbs catalysts (Grubbs et al., Angew. Chem., Ed. Engl. 34 (1995) 2039 and Organic Lett. 1 (1999) 953), which are ruthenium-benzylidene complexes. This relates to homogeneous catalysis. Heterogeneous catalysts have also been developed that are based on metals such as rhenium, molybdenum, and tungsten, deposited on alumina or silica.

Lastly, studies have been carried out for the production of immobilized catalysts, these being catalysts in which the active principle is that of the homogeneous catalyst, particularly the ruthenium-carbene complexes, but is immobilized on an inert support. The objective of these studies is to increase the selectivity of the cross metathesis reaction with regard to competing reactions such as the "homometathesis" reactions between the reactants brought together. The studies relate not only to the structure of the catalysts but also to the effect of the reaction mixture and the additives that may be introduced.

The cross metathesis reaction with ethylene during one of the steps of the first phase may be carried out with any active and selective metathesis catalyst, and is preferably conducted at a temperature of between 20 and 100° C. under a pressure of 1 to 30 bar in the presence of a conventional metathesis catalyst, of ruthenium type, for example. The reaction time is selected according to the reactants employed and so as to reach as close as possible to equilibrium of the reaction. The reaction is carried out under ethylene pressure. It may be carried out directly on the oil, the ester, and on the fatty acid.

The ruthenium catalysts are selected preferably from charged or uncharged catalysts of general formula:

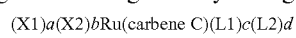

in which:
a, b, c and d are integers, with a and b being 0, 1 or 2, and c and d being 0, 1, 2, 3 or 4;
X1 and X2, which are identical or different, each represent a charged or uncharged unidentate or multidentate ligand; examples include halides, sulfate, carbonate, carboxylates, alkoxides, phenoxides, amides, tosylate, hexafluorophosphate, tetrafluoroborate, bis-triflylamide, tetraphenylborate, and derivatives. X1 or X2 may be bonded to Y1 or Y2 or to the (carbene C) so as to form a bidentate ligand (or chelate) on the ruthenium; and
L1 and L2, which are identical or different, are electron-donating ligands, such as phosphine, phosphite, phosphonite, phosphinite, arsine, stilbine, an olefin or an aromatic, a carbonyl compound, an ether, an alcohol, an amine, a pyridine or derivative, an imine, a thioether or a heterocyclic carbene.

L1 or L2 may be bonded to the "carbene C" so as to form a bidentate ligand or chelate.

The "carbene C" may be represented by the general formula: C_(R1)_(R2), for which R1 and R2 are identical or different, such as hydrogen or any other saturated or unsaturated, cyclic, branched or linear, or aromatic hydrocarbonyl group. Examples include complexes of ruthenium with alkylidenes, or with cumulenes, such as vinylidenes, Ru=C=CHR, or allenylidenes, Ru=C=C=CR1R2, or indenylidenes.

A functional group which enhances the retention of the ruthenium complex in the ionic liquid may be grafted onto at least one of the ligands X1, X2, L1 and L2, or onto the carbene C. This functional group may be charged or uncharged, such as, preferably, an ester, an ether, a thiol, an acid, an alcohol, an amine, a nitrogen-containing heterocycle, a sulfonate, a carboxylate, a quaternary ammonium, a guanidinium, a quaternary phosphonium, a pyridinium, an imidazolium, a morpholinium or a sulfonium.

The cross metathesis reaction with butyl acrylate is carried out under very well-known conditions. The reaction temperature is between 20 and 100° C., generally at atmospheric pressure, to allow easy release of the ethylene in the presence of a ruthenium-based catalyst of formula (I) as given above.

The reaction scheme of the synthesis of nitriles from acids, which is well-known to the skilled person, may be summarized as follows:

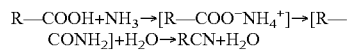

This scheme applies both to natural fatty acids (esters) and to ω-unsaturated fatty acids.

The process may be carried out batchwise in liquid or gas phase, or continuously in gas phase. The reaction is carried out at a high temperature >250° C. in the presence of a catalyst, which is generally a metal oxide and most commonly zinc oxide. Continuous removal of the water formed with entrainment, moreover, of the unreacted ammonia, enables rapid completion of the reaction.

The pyrolysis reaction employed in the variant of the process is carried out on the ester form of the relevant hydroxyl-containing fatty acid, in general the methyl ester. The reaction is carried out at high temperature, of between 400 and 750° C. and preferably between 500 and 600° C., in the presence of superheated steam.

The pyrolysis reaction, applied to methyl ricinoleate, corresponds to the following procedure:

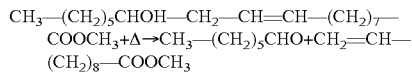

It is followed by an ammoniation:

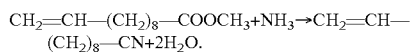

The step of synthesizing the fatty ω-amino acids (esters) from the fatty nitrile esters involves a conventional hydrogenation. There are many catalysts, though preference is given to using Raney nickels and cobalts. To promote the formation of primary amine, a partial pressure of ammonia is employed. Lastly, the reduction of the nitrile function to primary amine is well known to the skilled person.

In the process of the invention, the fatty acid may be treated either in its acid form or in its ester form, including triglyceride or diglyceride forms. The entirely commonplace switch from one form to the other, by methanolysis, esterification or hydrolysis, does not constitute a chemical conversion in the sense of the process.

All of the mechanisms detailed below illustrate the synthesis of the acids, in order to facilitate the account. However, metathesis is also effective with an ester and is even more effective, since the medium is generally more anhydrous. In the same way, the schemes illustrate reactions with the trans isomer of the acids (or esters); the mechanisms are equally applicable to the cis isomers.

The reaction mechanism of this reaction is illustrated by scheme 1 below.

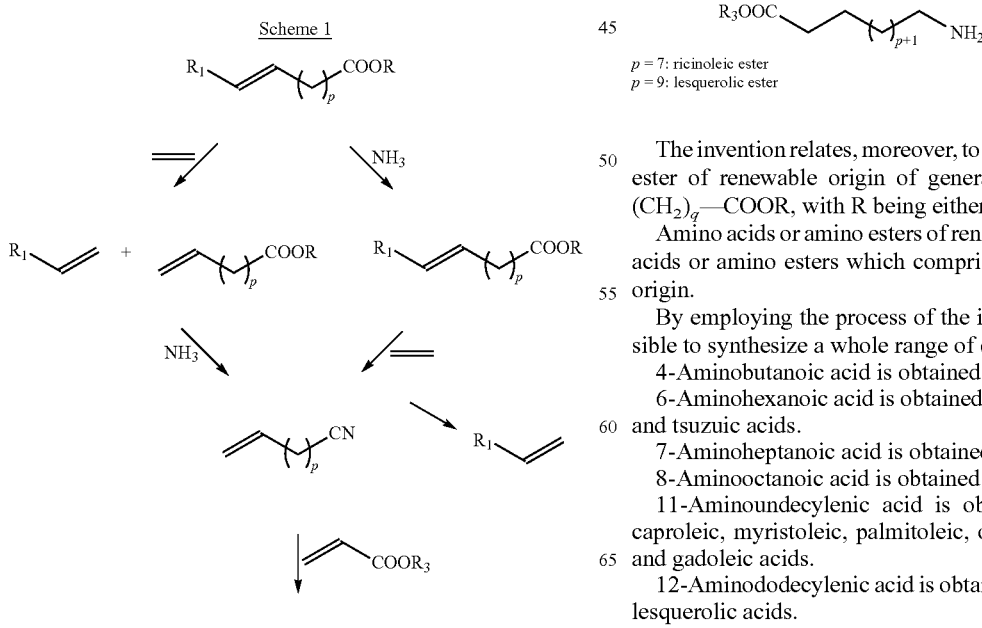

In the scheme above, $q=p+2$.

The implementational variant of the process of the invention, applied to hydroxyl-containing unsaturated fatty acids, is illustrated by scheme 2 below.

The invention relates, moreover, to the amino acid or amino ester of renewable origin of general formula $NH_2CH_2$—$(CH_2)_q$—COOR, with R being either H or a butyl radical.

Amino acids or amino esters of renewable origin are amino acids or amino esters which comprise carbon of renewable origin.

By employing the process of the invention it will be possible to synthesize a whole range of ω-amino acids.

4-Aminobutanoic acid is obtained from eicosenoic acid.

6-Aminohexanoic acid is obtained from obtusilic, linderic and tsuzuic acids.

7-Aminoheptanoic acid is obtained from physeteric acid.

8-Aminooctanoic acid is obtained from petroselinic acid.

11-Aminoundecylenic acid is obtained from lauroleic, caproleic, myristoleic, palmitoleic, oleic, elaidic, ricinoleic and gadoleic acids.

12-Aminododecylenic acid is obtained from ricinoleic and lesquerolic acids.

13-Aminotridecylenic acid is obtained from vaccenic, gondoic, cetoleic and lesquerolic acids.

15-Aminopentadecylenic acid is obtained from erucic acid.

The invention is illustrated by the examples which follow.

EXAMPLE 1

This example illustrates the first step of ethenolysis of methyl oleate according to the process that is the subject of the invention. For this reaction, the complex catalyst [RuCl$_2$(=CHPh)(IMesH$_2$)(PCy$_3$)] is used, whose formula (A) is given below. The reaction is carried out in CH$_2$Cl$_2$, at a concentration of 0.05 M methyl oleate and 0.2 Methylene, at a temperature of 55° C. and at atmospheric pressure, and for 6 hours, in the presence of the catalyst at a concentration of 5 mol % relative to the methyl oleate. The yields are determined by chromatographic analysis. It is possible to measure a yield of methyl 9-decenoate, CH$_2$=CH—(CH$_2$)$_7$—COOCH$_3$, and of 1-decene of 55 mol %.

Catalyst of Formula (A)

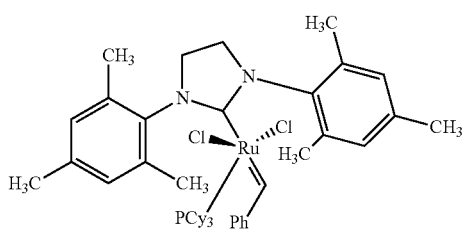

Formula (A)

EXAMPLE 2

This example illustrates the second step, of ammoniation, converting the 9-decenoic acid obtained after hydrolysis of the ester from the first step into nitrile of formula CN—(CH$_2$)$_7$—CH=CH$_2$ The ammoniation reaction of 9-decenoic acid (3.5 g) to form the ω-unsaturated nitrile of formula CN—(CH$_2$)$_7$—CH=CH$_2$ is carried out batchwise, with introduction of ammonia in a molar excess over the acid and at a temperature of 300° C. and at atmospheric pressure (in the gas phase), in the presence of a zinc oxide catalyst. The reactor is equipped with a condenser at 100° C. Ammonia is also injected continuously for 6 hours. The continuous removal of the water formed entrains the excess ammonia and allows rapid completion of the reaction. 2.6 g of the nitrile are recovered, and are separated by vacuum distillation.

EXAMPLE 3 (COMPARATIVE)

This example illustrates a cross metathesis reaction of a nitrile of formula CN—(CH$_2$)$_7$—CH=CH$_2$, obtained from the step of example 2, with methyl acrylate, according to the following reaction:

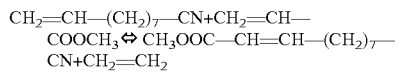

A 50 ml Schlenk tube is charged with 83 mg of 9-cyanodecene or 9-decenenitrile (0.55 mmol), 86 mg of methyl acrylate (1 mmol) and 10 ml of toluene distilled over sodium-benzophenone. This initial charge is admixed with 1.5 mg (2.4×10$^{-3}$ mmol) of second-generation Hoveyda-Grubbs catalyst [(1,3-bis(2,4,6-trimethylphenyl)-2-imidazolidinylidene)dichloro(o-isopropoxyphenylmethylene]ruthenium, sold by the Aldrich® company). Under nitrogen and with magnetic stirring, the reaction mixture is heated to 100° C. and left to react for 1 hour. It is analyzed by gas chromatography (dodecane standard). The conversion is 70%. The selectivity for methyl ester nitrile (cis+trans mixture) is 100%.

EXAMPLE 4

This example illustrates the variant with reversal of the order of the two steps of phase 1: ammoniation of the unsaturated fatty acid, then ethenolysis of the unsaturated nitrile.

The ammoniation of oleic acid is carried out batchwise, with introduction of ammonia in molar excess relative to the acid, and at a temperature of 300° C. and at atmospheric pressure (in the gas phase), in the presence of the zinc oxide catalyst. The continuous removal of the water formed entrains the excess ammonia and allows rapid completion of the reaction.

The ethenolysis of the nitrile of oleic acid is carried out at 60° C. under atmospheric pressure in the presence of a ruthenium-based catalyst, [RuCl$_2$(=CHPh)(IMesH$_2$)(PCy$_3$)], using an excess of ethylene, to give 9-decenoic acid, CH$_2$=CH—(CH$_2$)$_7$—COOH. The yields are determined by chromatographic analysis. At the end of the reaction, 6 hours, the C10 α-olefin is separated by vacuum distillation, to give the 9-decenoic nitrile CH$_2$=CH—(CH$_2$)$_7$—CN. The yields are determined by chromatographic analysis. It is possible to measure a yield of 55%.

EXAMPLE 5

Pyrolysis of Hydroxyl-Containing Fatty Acid

The triglyceride of ricinoleic acid is transesterified by excess methanol in the presence of sodium methoxide.

The ester is then evaporated at 225° C. and subsequently mixed with superheated steam (620° C.). The reaction is short, around ten seconds. The methyl undecenoate is subsequently purified, first by cooling of the mixture, which allows the extraction of water, and then by a series of distillations, that allows the separation of the ester and of the by-products of the reaction.

EXAMPLE 6

Cross metathesis, butyl acrylate-10-undecenenitrile

10-Undecenenitrile is purified beforehand over alumina (VWR Normapur basic alumina). 10 g of alumina are charged to a column, and 20 g of 10-undecenenitrile are percolated on the column at atmospheric pressure.

The metathesis reactor is a 250 ml double-wall glass reactor equipped with a magnetic stirrer, a condenser, a temperature probe, a nitrogen inlet, and a syringe driver for continuous addition of the metathesis catalyst.

After it has been purged with nitrogen, the reactor is charged with 5 g of 10-undecenenitrile (30 mmol), 7.6 g of butyl acrylate (60 mmol) and 50 g of toluene dried over molecular sieve. A syringe is charged with 0.5 mg of catalyst of formula (I) given above (catalyst supplied by the company UMICORE—7.5×10$^{-4}$ mmol—0.0025 mol % relative to the 10-undecenenitrile) in solution in 5 ml of toluene. The reaction mixture is heated to 100° C. and then the catalyst is added via the syringe driver over a period of 3 hours. The resulting reaction mixture is analyzed by gas chromatography to determine the conversion of 10-undecenenitrile and the selectivities for unsaturated C12 ester-nitrile (cross metathesis product) and for unsaturated C20 dintrile (self-metathesis product).

EXAMPLE 7 (COMPARATIVE)

Example 7 is carried out under the same conditions as example 6, but using the catalyst of formula (II) below in the same molar amount.

Formula (II)

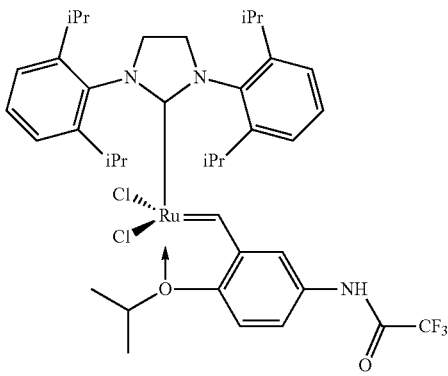

EXAMPLE 8 (COMPARATIVE)

Example 8 is carried out under the same conditions as example 6, but using the catalyst of formula (III) below in the same molar amount.

Formula (III)

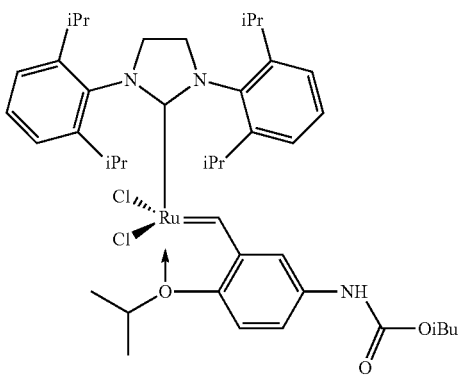

EXAMPLE 9 (COMPARATIVE)

Example 9 is carried out under the same conditions as example 6, but replacing the butyl acrylate by methyl acrylate in the same molar amount.

All of the results from examples 6 to 9 are summarized in table 1 below.

TABLE 1

| Example | Acrylate | Catalyst | Conversion (%) $C_{11}$ nitrile | Selectivity (%) $C_{12}$ ester-nitrile | Selectivity (%) $C_{20}$ dinitrile |
|---|---|---|---|---|---|
| 6 | ABu | Formula (I) | 63 | 66 | 34 |
| 7 | ABu | Formula (II) | 34 | 25 | 75 |
| 8 | ABu | Formula (III) | 21 | 26 | 74 |
| 9 | AMe | Formula (I) | 10 | 30 | 70 |

These results show that only the ABu/catalyst of formula (I) pairing produces good conversions and selectivities in cross metathesis at low catalyst content.

The invention claimed is:

1. A process for synthesizing an ω-amino acid (ester) of formula $R_3OOC—(CH_2)_q—CH_2NH_2$, in which $R_3$ is H or an n-butyl radical and q is an integral index of between 2 and 13, from a monounsaturated fatty acid (ester) of formula $(R_1—CH=CH—(CH_2)_p—COO)_xR_2$, in which x represents 1, 2 or 3, $R_1$ is H or a hydrocarbon radical comprising from 4 to 11 carbon atoms and, where appropriate, a hydroxyl function, $R_2$ is H or an alkyl radical comprising from 2 to 4 carbon atoms, and may contain one or more heteroatoms, and p is an integral index of between 2 and 11, comprising a reaction step of ammoniation, leading to the conversion of the carbonyl function to a nitrile function, wherein:

in a first stage, the unsaturated fatty acid/ester is converted into an ω-unsaturated nitrile of formula $CH_2=CH—(CH_2)_p—CN$ in two successive steps, in any order, ethenolysis and ammoniation, and then in a second stage, this ω-unsaturated nitrile is converted into an ester nitrile of formula $R_3OOC—CH=CH—(CH_2)_p—CN$, in which $R_3$ is n-butyl, by a cross metathesis reaction of the ω-unsaturated nitrile with an acrylate of formula $CH_2=CH—COOR_3$, with a catalyst of formula (I), (I)

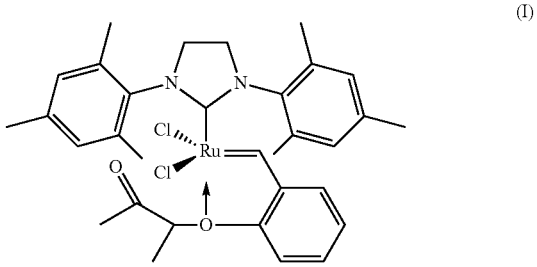

and then in a third stage, the ester nitrile is hydrogenated to ω-amino acid (ester) of formula $ROOC—(CH_2)_q—CH_2NH_2$.

2. The process as claimed in claim 1, wherein in the first stage the ethenolysis of the acid (ester) is carried out first, followed by the ammoniation of the ω-alkenoic acid.

3. The process as claimed in claim 1, wherein in the first stage, the ammoniation of the acid (ester) is carried out first, followed by the ethenolysis of the nitrile of the starting fatty acid.

4. The process as claimed in claim 1, wherein in the first stage the pyrolysis of the hydroxyl-containing fatty acid (ester) is carried out first of all, followed by the ammoniation of the ω-alkenoic acid (ester) obtained from the pyrolysis.

5. The process as claimed in claim 1, wherein in the first stage the ammoniation of the acid (ester) is carried out, without continuing to the ethenolysis reaction.

* * * * *